United States Patent
Manning et al.

(10) Patent No.: US 6,847,439 B2
(45) Date of Patent: Jan. 25, 2005

(54) APPARATUS AND METHOD FOR SYNCHRONIZING HIGH-SPEED OPTICAL MEASUREMENTS MADE OVER A RANGE OF WAVELENGTHS

(76) Inventors: William H. Manning, 105 Desert Brook Dr., Wrentham, MA (US) 02093; Michael Paul Minneman, 1275 W. 13th Ave., Broomfield, CO (US) 80020

( * ) Notice: Subject to any disclaimer, the term of this patent is extended or adjusted under 35 U.S.C. 154(b) by 243 days.

(21) Appl. No.: 10/060,452

(22) Filed: Jan. 30, 2002

(65) Prior Publication Data

US 2002/0101580 A1 Aug. 1, 2002

Related U.S. Application Data

(60) Provisional application No. 60/265,297, filed on Jan. 30, 2001.

(51) Int. Cl.[7] .............................................. G01N 21/00
(52) U.S. Cl. ..................................................... 356/73.1
(58) Field of Search ........................ 356/73.1, 39, 124, 356/125, 437, 326, 301, 318, 451; 250/227.18

(56) References Cited

U.S. PATENT DOCUMENTS 6,359,685 B1 * 3/2002 Colbourne et al. ......... 356/124

\* cited by examiner

*Primary Examiner*—Tu T. Nguyen
(74) *Attorney, Agent, or Firm*—Renner, Otto, Boisselle & Sklar, LLP

(57) ABSTRACT

A light instrumentation system for measuring optical power or intensity of an input as wavelength of the input varies with respect to a time includes a reference providing a detectable optical power or intensity upon encountering a wavelength having a prescribed value, and a detector system coordinated with the reference and providing a detectable feature for measuring the optical power or intensity. A method of testing an object using electromagnetic energy includes illuminating the object using electromagnetic energy while sweeping the electromagnetic energy over a range of wavelengths, measuring electromagnetic energy from the object in response to the illuminating, and coordinating the measuring step with one or more distinct wavelength points of the sweep determined by a wavelength dependent transmission device to which the electromagnetic energy is directed.

10 Claims, 5 Drawing Sheets

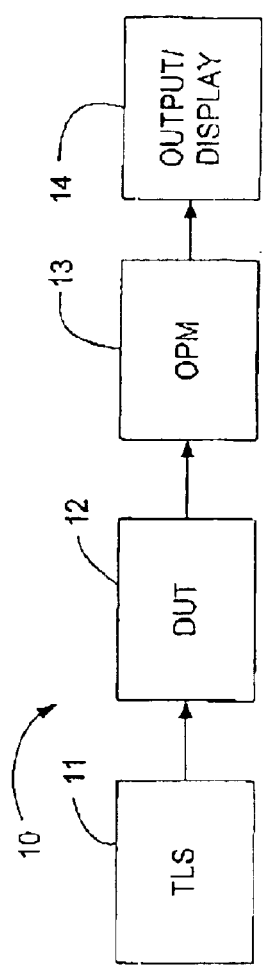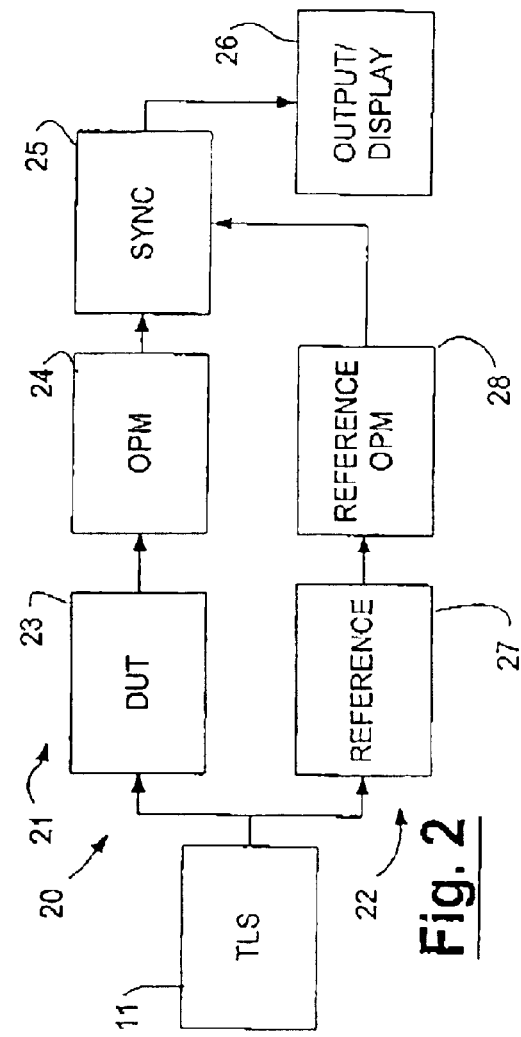

APPARATUS AND METHOD FOR SYNCHRONIZING HIGH-SPEED OPTICAL MEASUREMENTS MADE OVER A RANGE OF WAVELENGTHS

CROSS-REFERENCE TO THE RELATED APPLICATIONS

This application claims the benefit of U.S. Provisional Application Ser. No. 60/265,297, filed Jan. 30, 2001.

TECHNICAL FIELD

The present invention relates generally, as indicated, to data coordination method and apparatus, and more particularly, to apparatus and method for synchronizing high-speed optical measurements made over a range of wavelengths.

BACKGROUND

Optical signals are used for a variety of purposes. For example, optical signals may be used in the field of communications, the signals being transmitted via optical fibers and various other optical equipment, such as switching equipment, multiplexers, amplifiers, and the like. Optical signals also are used in measurement systems, detector systems, and the like. There is a need to test the various optical fibers and other equipment. Often the testing involves the transmitting, reflecting or absorbing of light at one or more wavelengths and measuring light at one or more wavelengths.

Optical power meters (and many other light measuring instruments) generally do not discriminate wavelengths; rather they measure light intensity or optical power independently or substantially independently of wavelength. Therefore, it is necessary to associate a wavelength with the respective measurements. In prior light measuring instruments, which have used a scanning light source to provide incident illumination to a device under test (DUT), the source also has been used to provide to the measuring circuitry electrical signals that identify the wavelength of the light being supplied the DUT and, thus, allegedly then being measured. In some light measuring instruments the operator would manually provide an input to identify the wavelength of the light being supplied. A disadvantage to these approaches is the need for a direct relationship, indeed, a dependence, of the light source and the measuring circuitry so the electrical signals (from the light source) accurately identify wavelength and can be accurately construed (by the measuring circuitry) to identify wavelength. Although such direct relationship may not be difficult for light sources and measuring circuits manufactured by the same company, achieving such direct relationship is difficult and even may be impossible if the light source and measuring circuitry are manufactured by different companies. As improved and/or different light sources are and become available from a number of companies, such association becomes difficult, if not impossible, and may lead to errors in the output measurements of optical power/light intensity with respect to wavelength of the measured light. In an example using such a measuring instrument, the wavelength of incident light may be scanned over a range from 1520 nm (nanometers) to 1560 nm, over a period of about one second; and measurements may be made at a rate of from a few to 100,000 per second. Due to inaccuracy in coordination, such as are mentioned above, wavelength error on the order of hundreds picometers between the actual incident wavelength and the output data indicating optical power measurement made have been found to occur. There may be other larger or smaller inaccuracies in various measuring instruments. Thus, there is a need for better correlation or coordination of such intensity or optical power measurements with respect to the wavelength(s) of light at the point the respective measurements are taken.

Typically, to test optical components with narrow wavelength features, a tunable laser source is swept across a wavelength band, and the photonic performance of the component is monitored at a large number of wavelengths. In FIG. 1 an exemplary prior art optical test or measuring system 10 includes a tunable laser source (sometimes referred to as "TLS") 11, a device under test (sometimes referred to as "DUT") 12, an optical power meter (sometimes referred to as "OPM") 13, and an output circuit and/or display 14, which may display the measurement data, use the measurement data, etc. Usually the optical power meter 13 itself and/or the photosensor thereof measures light power or intensity without regard to wavelength, and, therefore, coordination or synchronization of the tunable laser source 11 with the OPM 13 is necessary so the light power or intensity measurement data is coordinated with the wavelength of light provided the DUT 12 and being measured. More specifically, to create an accurate model of the performance of the DUT across the wavelength band over which the DUT is being tested, it is necessary to know the wavelength of light being measured for each measurement. In the past several techniques have been used to provide such coordination. In one conventional approach the TLS 11 is stepped to produce respective wavelengths at specific time periods, and the OPM 13 is coordinated with those time periods so the measurement at a given time period represents the measurement with respect to a corresponding output wavelength by the TLS. However, such systems are relatively slow and to an extent inaccurate because there is a need to provide a wait state or time period during each step while the TLS provides a particular wavelength output and the OPM makes the necessary measurement and because measurements are not made at wavelengths between respective steps. Accordingly, there is a need to improve the speed and accuracy or completeness of such optical measurements.

Another conventional approach to coordinating the measurements made by the OPM 13 with the wavelength of light from the TLS 11 has to been to provide tight synchronization between the TLS wavelength sweep with the measurement so the timing of the measurement can be used to determine the wavelength being presented at each measurement. Still another approach has been to provide direct so-called real-time communication between the TLS 11 and the OPM 13, with the TLS informing the OPM of the wavelength at each measurement time. However, both these approaches are somewhat inaccurate due to latency, that is, the delay in time required to communicate wavelength information from the TLS to the OPM and/or for the OPM to respond to the information indicative of the TLS wavelength. Another inaccuracy encountered in these and other systems may occur due to the non-linearity of the TLS wavelength sweep, that is, the change in wavelength of the TLS output over a period of time may be non-linear. Also, such non-linearity may be different for different laser sources (or other light sources) thus requiring complex and time consuming calibrations and also may vary with certain relatively uncontrolled conditions such as, for example, aging, various ambient conditions, such as temperature, pressure, humidity, and so forth. Although these approaches to coordination may be faster than the step coordination mentioned above, nevertheless, there is a need for improving the accuracy and reliability of the coordinating of the measurements made by the optical measurement systems with wavelength of the illuminating source.

The terms electromagnetic energy, light, optical, laser, laser output, and the like, are terms used herein. Such terms identify, broadly, electromagnetic energy that may be in part or all of the visible spectrum, the infrared, near-infrared and far-infrared spectra, and ultraviolet spectrum, and/or the like. Thus, reference to such terms indicates those wavelengths of electromagnetic energy operable in the context of the invention.

Accordingly, there is a need to obtain meaningful measurements of electromagnetic energy, e.g., with respect to wavelength, using a light source and measuring circuitry that are independent of each other.

There also is a need to improve the accuracy of optical power measurements with respect to wavelength of the incident electromagnetic energy.

SUMMARY

Briefly, according to an aspect of the invention, improved correlation is provided between measurement data representative of electromagnetic energy and wavelength.

Another aspect relates to coordinate or in a sense to synchronize a tunable laser source with intensity, optical power or like measurements made in an optical measurement instrument using wavelength fence post timing or coordinating pulses.

Another aspect relates to use of a periodic wavelength reference in conjunction with a measurement system to obviate the need to time synchronize measurements with a tunable laser source.

According to an aspect of the invention, an optical measuring apparatus includes an optical scanning system for supplying to a device under test electromagnetic energy at a plurality of periodically varying wavelengths, a measuring circuit for measuring electromagnetic energy from the device under test, and a synchronizer, including a device responsive to the electromagnetic energy from the optical scanning system to provide a known response to one or more wavelengths of the electromagnetic energy to synchronize the measuring circuit with the optical scanning system.

According to another aspect, an optical testing instrument includes a tunable illumination source for illuminating a device under test using electromagnetic energy having a wavelength that is swept over a wavelength band, a wavelength dependent transmission responsive device to determine one or more distinct wavelength points in the sweep of the illumination source, and a measuring circuit synchronized to the wavelength dependent to measure illumination from the device under test over at least a range of the wavelength band.

According to another aspect, a method of testing an object using electromagnetic energy includes illuminating the object using electromagnetic energy while sweeping the electromagnetic energy over a range of wavelengths, measuring electromagnetic energy from the object in response to such illuminating, coordinating the measuring step with one or more distinct wavelength points of the sweep determined by a wavelength dependent transmission device to which the electromagnetic energy is directed.

According to another aspect, a system for measuring electromagnetic energy from a device under test that is illuminated with electromagnetic energy at a wavelength that is swept over a range of wavelengths includes a measuring system for measuring electromagnetic energy from the device under test, and a periodic wavelength reference having a detectable distinct response to a distinct wavelength of such electromagnetic energy to indicate to the measuring system occurrence of such distinct wavelength as a reference point to synchronize measurements with the sweeping of the wavelength of the electromagnetic energy.

According to another aspect, a light instrumentation system for measuring optical power or intensity of an input as wavelength of the input varies with respect to a time includes a reference providing a detectable optical power or intensity upon encountering a wavelength having a prescribed value, and a detector system coordinated with the reference and providing a detectable feature for measuring the optical power or intensity.

According to another aspect, an apparatus for coordinating a series of optical measurements of an object illuminated by a tunable or scanning light source is characterized in that the tunable light source illuminates the object over a number of wavelengths while measurements with respect to the object are made to obtain respective data points, and the tunable laser source illuminates a reference of which measurements are taken to provide wavelength reference points with which to coordinate the data points obtained by measurements of the object.

According to another aspect, a method for coordinating a series of optical measurements of an object illuminated by a tunable or scanning light source, is characterized in that the tunable light source illuminates the object over a number of wavelengths while measurements with respect to the object are made to obtain respective data points, and the tunable laser source illuminates a reference of which measurements are taken to provide wavelength reference points with which to coordinate the data points obtained by measurements of the object.

A number of features are described herein with respect to embodiments of the invention; it will be appreciated that features described with respect to a given embodiment also may be employed in connection with other embodiments.

The invention comprises the features described herein, including the description, the annexed drawings, and, if appended, the claims, which set forth in detail certain illustrative embodiments. These embodiments are indicative, however, of but a few of the various ways in which the principles of the invention may be employed.

Although the invention is shown and described with respect to illustrative embodiments, it is evident that equivalents and modifications will occur to those persons skilled in the art upon the reading and understanding hereof. The present invention includes all such equivalents and modifications and is limited only by the scope of the claims if appended hereto.

BRIEF DESCRIPTION OF DRAWINGS

In the annexed drawings:

FIG. 1 is a schematic block diagram of a prior art measuring system;

FIG. 2 is a schematic block diagram of a measuring system according to the present invention;

DESCRIPTION

Figure 3:
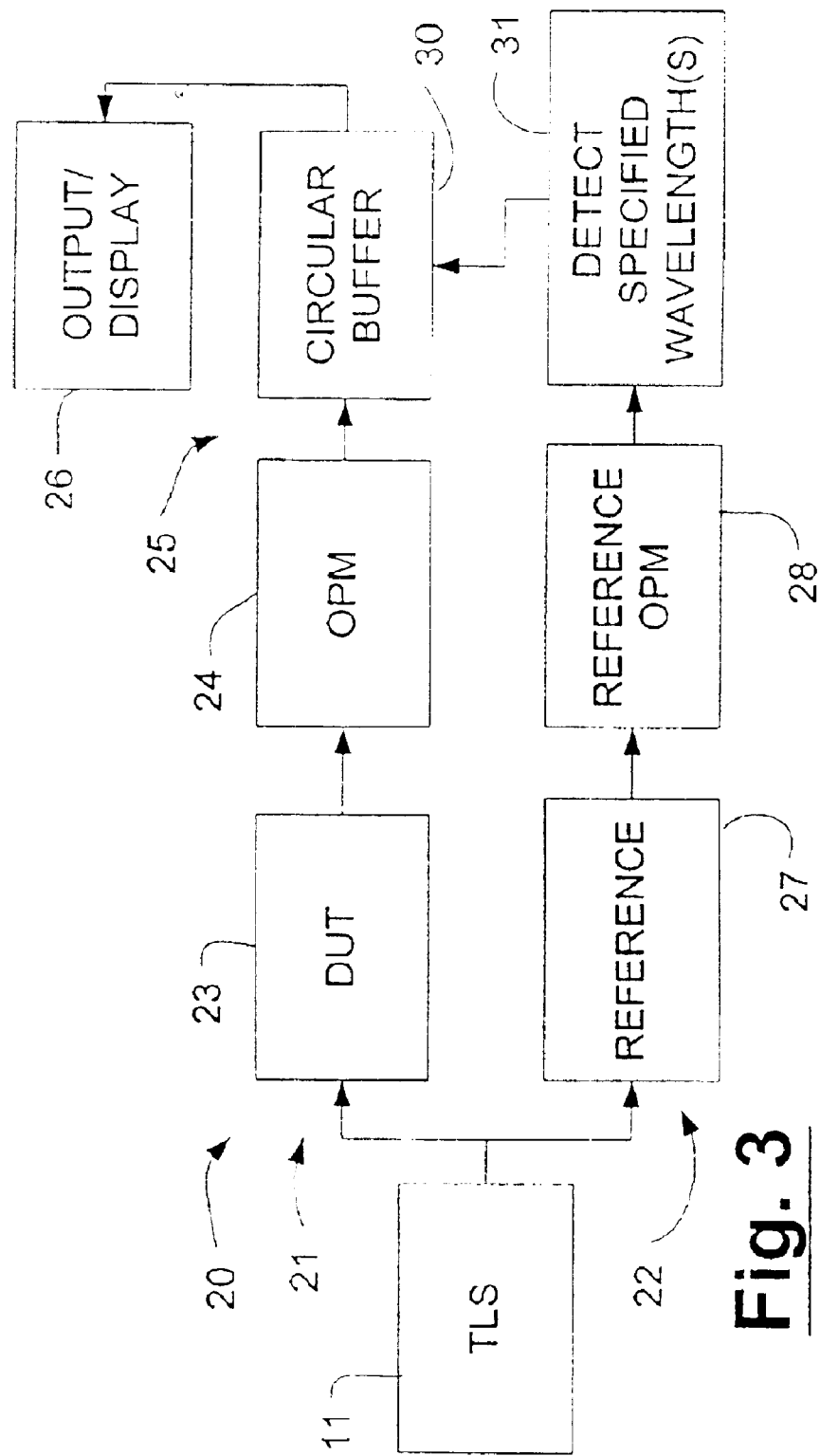
FIG. 3 is a more detailed schematic block diagram of the measuring system of FIG. 2.

Referring in detail to the drawings, where in like reference numerals designate like parts in the several figures, and initially to FIG. 2 (FIG. 1 was described above with respect to background information), a measuring system in accordance with the present invention is generally indicated at 20. The measuring system 20 includes a test measurement channel 21 and a reference measurement channel 22. A tunable laser source (TLS) 11, or some other suitable source of electromagnetic energy, provides incident light to both measurement channels. For brevity, the incident electromagnetic energy that which is measured will be referred to as "light" although it will be appreciated, as was mentioned above, that the electromagnetic energy may be other than light or visible light and may be in various wavelength ranges.

The measurement channel 21 includes a device under test (DUT) 23, such as, for example, an optical fiber, although it will be appreciated that other devices may be tested using the measuring system 20. The measurement channel 21 also includes an optical power meter (OPM) 24 and a synchronizing or coordinating device 25, described further below. One non-limiting example of an OPM in a measurement instrument of the type described may measure light intensity or optical power in a range of from on the order of −7 dB to on the order of about −45 dB or even −50 dB. An output circuit 26, which may include a display, if desired, or some other circuitry, storage, or means to utilize data representing measurements made by the measuring system 20 may be provided at the output of the measuring system.

The reference measurement channel 22 includes a reference 27 and a reference OPM 28. Both the DUT 23 and the reference 27 receive incident or input light from the TLS 11 and the reference OPM 28 measure light from the respective DUT and reference.

The synchronizing device 25 of the measuring system 20 synchronizes the measurement data from the OPM 24 with information representing wavelength as detected by the reference OPM 28. The synchronized data is provided the output circuit 26.

In using the measuring system 20 the TLS 11 provides input light to the DUT 23 and reference 27 in the respective test and reference measurement channels 21, 22. The reference 27 provides a known spectral response. For example, the reference 27 may be known to absorb some or all light at one or more wavelengths and to transmit some or all light at one or more other wavelengths. The TLS 11 provides light input to both measurement channels simultaneously. The synchronizing device 25 synchronizes or coordinates the measurement data from the test measurement channel 21 with one or more known responses provided by the reference measurement channel 22 to the synchronizing device. Therefore, when the reference measurement channel 22 provides a known response indicating a given wavelength of the TLS 11, the data then provided by the test measurement channel 21 to the synchronizing device 25 is known to be a measurement at such wavelength. If the reference measurement channel 22 provides multiple known responses representative of respective wavelengths provided by the TLS 11, those known responses can be used by the synchronizing device 25 to coordinate the data from the test measurement channel 21 with those respective wavelengths. Based on such synchronization and knowing the laser sweep characteristic, timing and/or the like, timing of subsequent measurements and/or other synchronizing points provided by the reference measurement channel 22, other measurement data also can be coordinated with wavelength as is described further below. Accordingly, the data provided the output 26 represents the measurements made in the test measurement channel 21 for respective wavelengths as coordinated by the synchronizing device 25 with respect to measurements made in the reference measurement channel 22.

In one example, the reference 27 is a gas. The gas is contained in a container, such as a test cell, and light from the TLS 11 is transmitted through the gas reference. As is well known, respective gases have one or more respective light absorption peaks; and these can be detected by the reference OPM 26. As the TLS 11 supplies light simultaneously to both the test channel 22 and the measurement channel 21, the sensing of a respective absorption peak sensed by the photosensor of the reference OPM 28 occurs at the same time that the photosensor of the DUT OPM 24, for example, is sensing light at the wavelength of that absorption peak. Therefore, such absorption peak identifies the wavelength of light being sensed at that time by the DUT OPM 24, and, thus, such absorption peak allows for coordination or synchronization of the DUT measurement data with the wavelength of light provided by the TLS 11 during the sweep of the TLS wavelength over the particular range of wavelengths it produces. It will be appreciated that the reference 27 may be other than a gas. Moreover, the reference 27 may be a Fabry Perot interferometer or other similar device.

Summarizing, then, and as is described further below, the invention utilizes a reference, such as a periodic wavelength reference, several nonlimiting examples of which are a gas cell or a Fabry Perot device, that sets up fence posts or reference points in conjunction with a measurement system to obviate the need to synchronize the measurement with a tunable laser. For example, a periodic wavelength reference determines distinct wavelength points of the sweep if the input tunable laser; and this allows the measurement system to avoid any direct information from the tunable laser source to the measurement system by allowing the measurement system to determine the wavelength independently.

Further summarizing, and as also is described further below, in an embodiment of the invention the tunable laser source is generally set to sweep from a start wavelength to an end wavelength in a specified time. In the measurement system, a specific number of measurements are established, e.g., number of measurements per sweep, based on the user's wavelength resolution requirements. If the measurement system contains a wavelength referencing device (such as, but not limited to, a gas reference cell or a Fabry Perot device), it can determine the point in the sweep when the wavelength matches a feature of the reference, such as an absorption peak (or minimum). By continuously measuring until the point is reached, the measurement system can discard all measurements prior to that point at which the tunable laser source began sweeping (point of alignment with the wavelength reference minus measurement rate times the wavelength tuning rate), thus resulting in a set of measurements that aligns with the sweep of the tunable laser source without any independent information communicated between the tunable laser source and the measurement system. This can both reduce wavelength errors and the cost of implementing the measurement system.

Referring to FIG. 3, the synchronizing device 25 is shown in connection with the OPM 24 and the reference OPM 28. The synchronizing device includes a circular buffer 30, which receives sequentially data representing measurements by the OPM 24. The OPM may make a series of sequential measurements, for example, at the rate of a few per second, even 10,000 per second, still even 100,000 per second, or at some other rate and the circular buffer 30 receives and stores the respective measurements at respective buffer locations or memory locations. As a new datum is provided the circular buffer, the data already stored is sequenced to the next respective memory locations, and so forth. When the circular buffer is full, the oldest data is emptied to leave room for the next sequencing. Another type of circular data buffer is simply a memory having respective memory locations in which data is provided for storage; a processor and/or other conventional circuitry with appropriate programming, known to those who have ordinary skill in the art, can selectively deliver data for storage, retrieve data for readout, use or the like, and rewrite data, e.g., to update data or to store new data, with respect to such memory locations.

The synchronizing device 25 also includes a detector 31. The detector 31 detects specific characteristics of the data measured by the reference OPM 28. For example, the detector 31 may detect specified peak signals, i.e., signals that exceed a predetermined magnitude either in a positive or negative sense, which represent a prescribed light transmission or light absorption peak caused by the reference 27 as the input light from the TLS 10 is provided to the reference. As the respective peaks indicate respective wavelengths, information or signals indicating the detecting of those peaks is provided by the detector 31 to the circular buffer 30 (or to a device to read out the data in the data buffer) to indicate that the data stored in the buffer at the same time or point that the peak is detected represents a measurement by the OPM 24 at the given wavelength represented by the detected peak. Since the detected peak and the data from the OPM 24 represent a measurement at the given wavelength, and since the sweep rate or frequency of the TLS 11 are known, the wavelengths at which subsequent measurements by the OPM 24 are made will be known with substantial accuracy. Moreover, if the detector 31 detects several peaks during a sweep of the TLS, one peak at one given wavelength and another peak at another given wavelength, then the detection of each of those peaks may be used further to coordinate the data from the OPM 24, which is provided the circular buffer 30. The measurement data in the circular buffer 30 is coordinated with the wavelength of the light provided by the TLS and can be provided to the output 26, for example, as intensity or power is measured by light at a given wavelength that is input to the DUT.

Figure 4:
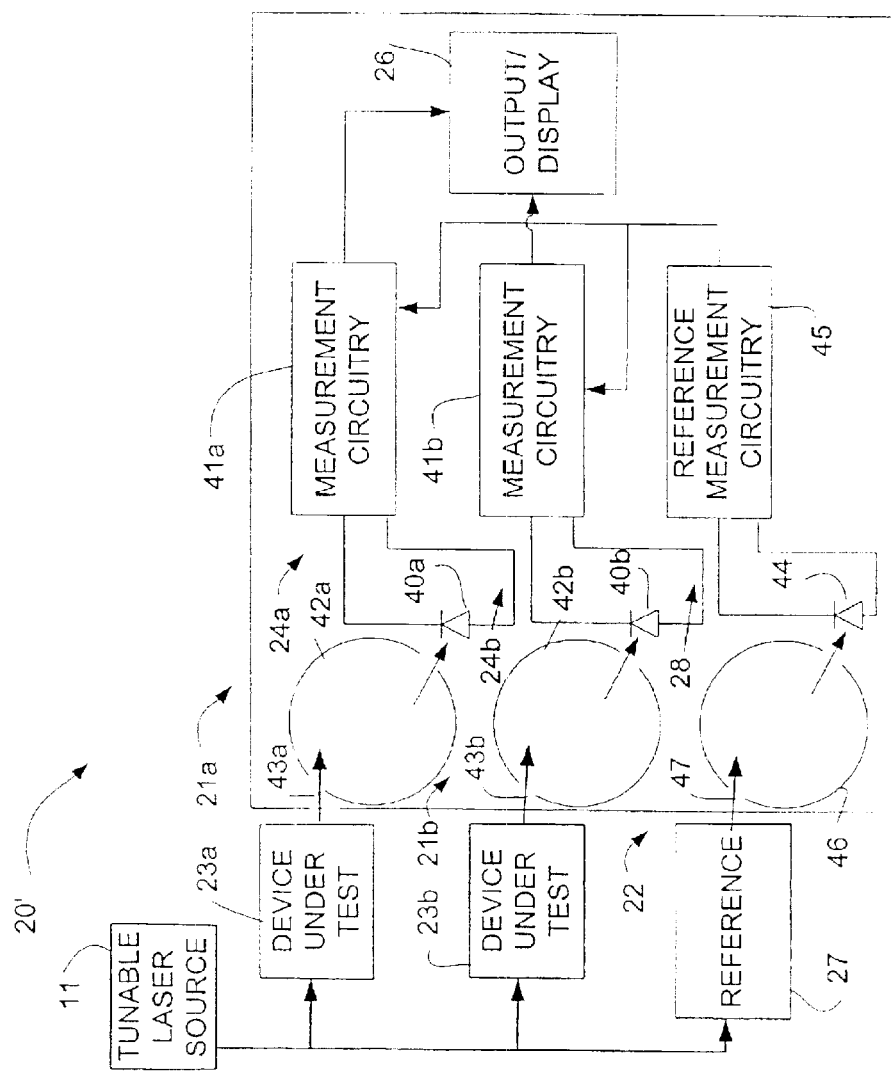
FIG. 4 is a schematic system diagram of a multiple measuring channel measuring system according to an embodiment of the invention.

Briefly referring to FIG. 4, a measuring system 20' is illustrated. The measuring system 20' is similar to the measuring system 20 described above, except the system 20' has a number of test measurement channels 21a, 21b (two are shown, but there may be more than two, if desired). The reference measurement channel 22 is coupled to each of the test measurement channels 21a, 21b to provide synchronization of the type described above. The respective OPM 24a, 24b in each measurement channel 21a, 21b includes a photosensor 40a, 40b and measurement circuitry 41a, 41b. The circular buffer 30 of the synchronization device 25 (FIGS. 2 and 3) is included in each measurement circuitry 41a, 41b. The photosensors may be conventional devices, which produce a detectable response, e.g., an electrical response, representative of light incident thereon. An example of a photosensor is an indium gallium arsenide photodiode. An optical integrating sphere 42a, 42b in each test measurement channel may receive light input 43a, 43b from a respective DUT 23a, 23b and provides light to the respective photosensor for detection as a representative characteristic of the respective DUT, for example. The reference measurement channel 22 OPM 28 in the measuring system 20' includes a reference photosensor 44, reference measurement circuitry 45 and an integrating sphere 46 to detect and to measure the light input 47 received from the reference 27. The detector of specified wavelength(s) 31 (FIG. 3) is included in the reference measurement circuitry 45. The reference measurement channel 22 provides inputs to the measurement circuitry 41a, 41b in the respective test measurement channels 21a, 21b to coordinate or to synchronize the measurement data with respect to the wavelength of the TLS 11. Thus, it will be appreciated that the measuring system 20' allows for simultaneous or, if desired, separate testing of respective DUTs 23a, 23b in respective test measurement channels 21a, 21b and the measurement data in the respective test measurement channels is synchronized or coordinated with the reference measurement data from the reference measurement channel 22, as was described above, for accurate representation of the data with regard to respective wavelengths at which the data was taken.

The output circuit and/or display 26 illustrated in the measuring system 20' of FIG. 4 may be coupled to a number of the test measurement channels 21a, 21b, etc. to provide output information indicative of the measurements made in several of those channels and/or to use that information. Alternatively, each test measurement channel 21a, 21b, for example, may have a respective output circuit and/or display 26 associated therewith.

Figure 5:
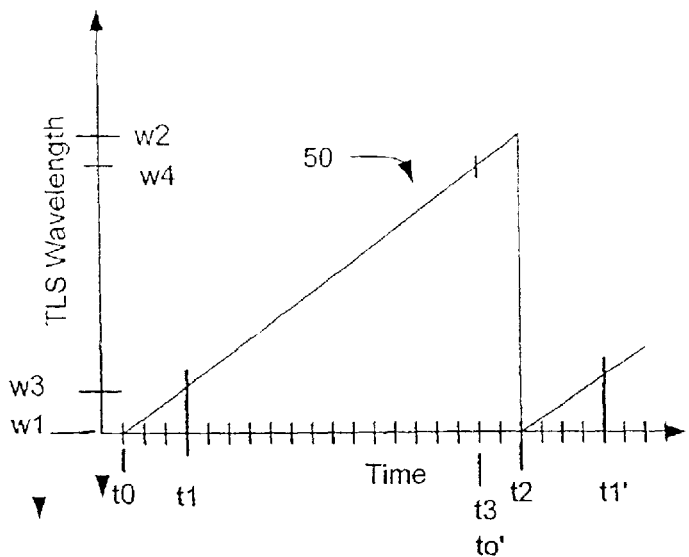
FIG. 5 is a graph showing a curve of light wavelength with respect to time for an ideal tunable or swept light source.
Figure 6:
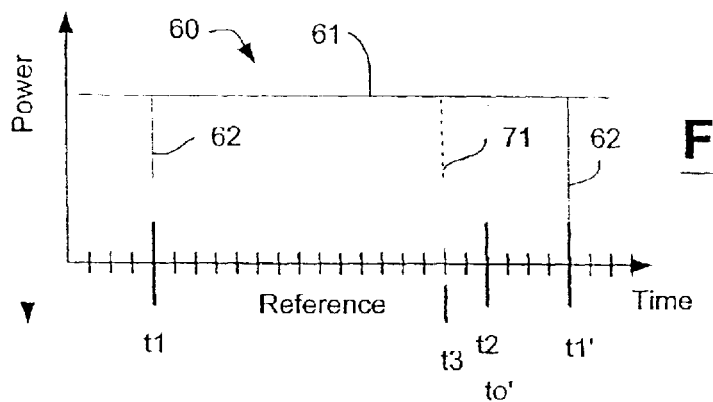
FIG. 6 is a graph that illustrates schematically a curve which represents the intensity or power measured in the reference measurement channel of the invention with respect to time as used with the light source represented in FIG. 5.
Figure 7:
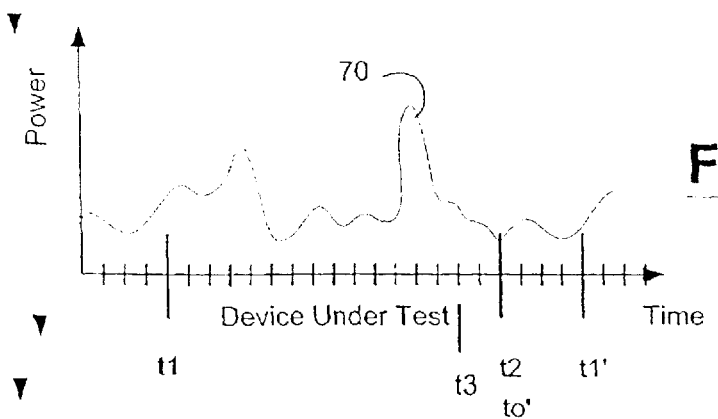
FIG. 7 is a graph illustrating a curve representing optical power or intensity with respect to time as measured in one of the test measurement channels of the invention as used with the light source represented in FIG. 5.

Turning to FIGS. 5, 6 and 7, operation of a measuring system 20, 20' in accordance with the invention is illustrated schematically. In FIG. 5 is illustrated a graph showing a curve 50 representing an ideal TLS 11 that provides a light output initially at a first wavelength w1; and the wavelength is swept linearly over time to a wavelength w2 (at time t2). Such wavelength sweep is repeated over respective time periods, as is represented by the curve 50 and the respective time periods from time to until time t2; t0' until time t2' (not shown), etc. FIG. 6 is a graph that illustrates schematically a curve 60, which represents the intensity or power measured in the reference measurement channel 22 with respect to time, as light from the TLS 11 is provided the reference 27 and is measured by the reference OPM 28.

The graph of FIG. 6, which represents optical measured in the reference measurement channel 22, is time coordinated with the graph of FIG. 5. Therefore, as can be seen in the curve 60 in FIG. 6, the optical power measured in the reference measurement channel 22 remains relatively constant (curve portion 61) in this example, except that at time t1 there is substantial reduction in measured optical power or intensity; which represents an absorption peak 62. The time between each successive absorption peaks 62, as represented on the X-axis of the graph of FIG. 6, may represent the time over which one or, more likely, a number of measurements of optical power is made by the reference OPM 28. Additional absorption peak 71 is discussed below and is ignored in the instant example. The nature of the reference 27 is known. Therefore, the wavelength w3 at which that absorption peak is known. Therefore, the wavelength of the light being measured at that time in the one or more measurement channels 21, 21a, 21b, etc., also is known.

In FIG. 7, which is time coordinated with the illustrations of FIGS. 5 and 6, is a graph illustrating a curve 70 representing optical power or intensity with respect to time as measured in one of the test measurement channels 21, for example.

As measurements of optical power are made in the test measurement channel 21, the measurement data is provided the circular buffer memory. However, such data is not provided to the output circuit 26 until the data is coordinated or synchronized with the wavelength of the light being measured. Such coordination occurs at time t1 when the absorption peak 62 is detected by the detector 31 (FIG. 3). At that point, the circular buffer memory and/or other circuitry associated therewith provides the instant and subsequent sequential data from the circular buffer memory to the output circuit 26. The data that was provided the circular buffer memory prior to the time t1, i.e., the point at which the absorption peak 62 occurs, may be discarded.

Data from the circular data buffer can be stopped from being presented to the output circuit 26 based on several possible occurrences, and then it can be restarted again at the next time t1', etc., in each sweep cycle of the TLS 11, as the absorption peak 62 is encountered. For example, the data can be stopped based on the amount of time it takes the TLS 11 to complete its wavelength sweep following occurrence of the wavelength at which the absorption peak 62 occurs. Therefore, when the TLS reaches its maximum wavelength upon expiration of a given sweep time period, the data from the circular buffer memory 30 would stop being provided the output circuit 26 until the occurrence of the next detection of the absorption peak 62, e.g., at time t1'. As an alternative, the point at which data would stop being provided by the circular buffer to the output circuit 26 may be prior to completion of a TLS wavelength sweep; this point may be set to avoid the possibility of an overshoot whereby upon the substitution of a different light source, the time frame for a complete sweep may be shorter than that of a different light source. Thus, it will be appreciated that the invention provides for the correlation or coordination of data points made using one or respective OPMs 24 with wavelength, this being based on the wavelength fence posts or known wavelength points provided by the reference 27 in the reference measurement channel 22.

As another alternative, measured optical power data provided the circular buffer 30 after the initial detection of the absorption peak 62 may continue to be provided to the output circuit 26 even as and following the end of one TLS wavelength sweep and beginning of the next TLS wavelength sweep. In such case, each time subsequent absorption peaks 62 are detected, the data can be re-synchronized or re-coordinated with that absorption peak and the wavelength it represents, e.g., by slightly spreading or compressing the measured optical power data to correspond as well as possible with the TLS wavelength. However, although this alternative avoids data loss, for example, from time t2 until the next absorption peak detection at time t1', etc., there is inherent inaccuracy as measurement data may be spread or compressed relative to actual wavelength.

Still a further alternative to stop data from the circular buffer 30 from being provided the output circuit 26 is to use a subsequent absorption peak obtained from the reference 27. An example of such a subsequent absorption peak is illustrated at 71 in FIG. 6, and the time of its occurrence is designated t3 in FIGS. 5, 6 and 7. Thus, upon detecting the occurrence of the subsequent absorption peak 71, the detector 31 may provide a signal to the circular buffer 30 or to associated circuitry to stop providing measured optical power data to the output circuit 26 until the next occurrence of the absorption peak 62. In this alternative the reference 27 may have the desired characteristics of providing the absorption peaks at the specified wavelengths represented by the absorption peaks 62 and 71. Alternatively, the reference 27 may be specifically designed to have those characteristics.

It will be appreciated, then, that the measurement data from the test measurement channels may be coordinated with the absorption peaks or other characteristics of the reference 27.

Figure 8:
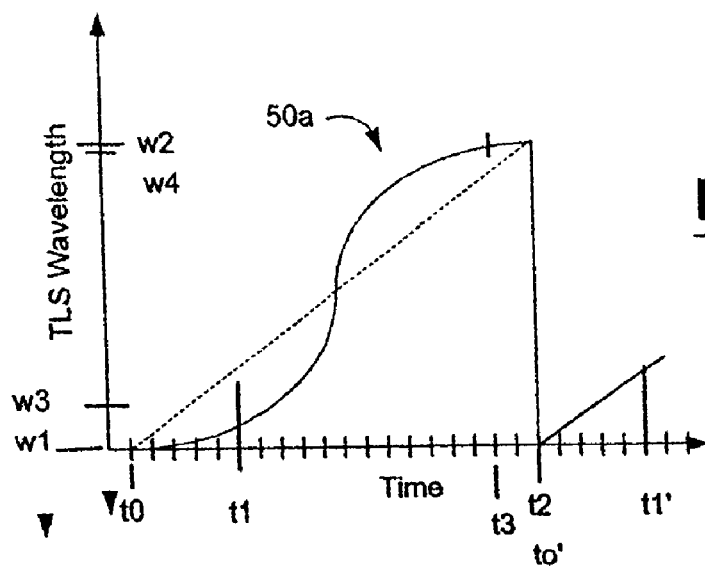
FIGS. 8, 9 and 10 are graphs, respectively, similar to those illustrated in FIGS. 5, 6 and 7 but depicting the invention as used with a tunable or swept light source which has a non-linear wavelength output with respect to time.
Figure 9:
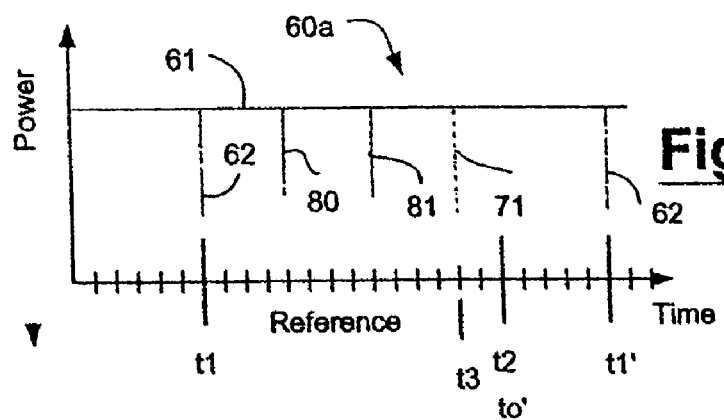
Figure 10:
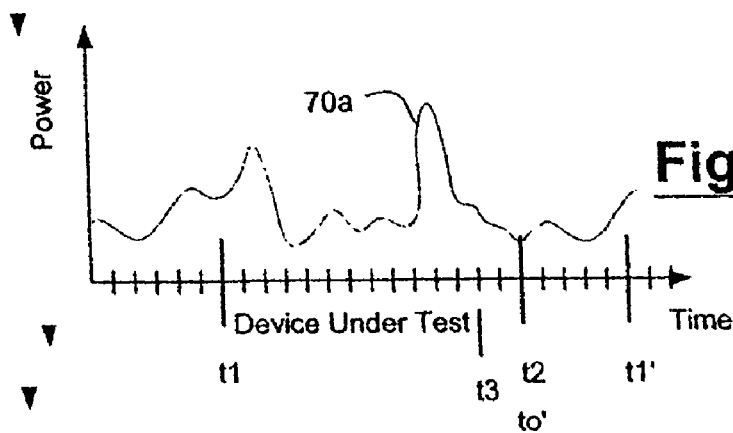

Referring briefly to FIGS. 8, 9 and 10, another set of graphs 50a, 60a, 70a, similar to those graphs illustrated in FIGS. 5, 6, and 7 is illustrated to demonstrate a circumstance in which the wavelength sweep of the TLS 11 is non-linear with respect to time. The present invention can be used to provide additional coordination or synchronizing points 80, 81 at which wavelengths additional absorption peaks are provided by the reference 27 and are detected by the reference OPM 28, including the detector 31. The absorption peaks 62, 71 may be used as described above with respect to the embodiment represented by FIGS. 5, 6 and 7; and the additional absorption peaks 80, 81 may be used to provide additional indications of respective wavelengths at which concurrent measurements from one or more DUTs are being made. By using a reference 27 that provides a plurality of absorption peaks that can be detected, the measurement data representing optical power of light from a DUT and the wavelength of that light can be obtained even for non-linear wavelength sweeping or scanning light sources (TLS) with a greater degree of accuracy than was previously possible. For example, the optical power or intensity measurements by one or respective OPM's in measurement channels 21, 21a, 21b, etc., can be coordinated with wavelength of the light source, e.g., the TLS 11, with good accuracy, whether light source sweep is linear or non-linear with respect to time or some other parameter.

In the past the TLS may be triggered to begin a wavelength sweep. However, due to latency, the actual sweep may not begin until a finite time after the trigger. The present invention does not have to rely on such trigger. Rather, the present invention uses a reference to provide one or a number of wavelength fence posts, such as the peaks 62 and 71, that are used for coordinating the optical measurements made by one or more OPMs. The fence posts are provided in real time based on the actual wavelength of the light provided by the TLS. As the number of wavelength fence posts increases, more points for coordination of optical power measurement data may be provided. The wavelength fence posts are provided without regard to the latency issues mentioned above because the wavelength fence posts are provided based on actual wavelength, not on a signal intended to cause the TLS to provide a given wavelength. Additionally, as was mentioned above, the wavelength fence posts provide for data coordination, rather than actual timing synchronization; and the wavelength fence posts can be used to provide such coordination even if the wavelength of the TLS output is nonlinear with respect to time during a given scan. Still further, the wavelength fence posts data coordination function may be substantially independent of the light source used by the measurement instrument 20, 20', provided optical profile or optical characteristics, e.g., absorption minima or absorption signals at respective values for respective wavelengths, occur at wavelengths of light provided by the light source, such as the TLS, in the measurement instrument.

INDUSTRIAL APPLICATION

It will be appreciated that the invention may be used to make optical measurements.

What is claimed is:

1. An optical testing instrument, comprising
    a tunable illumination source for illuminating a device under test using electromagnetic energy having a wavelength that is swept over a wavelength band,
    a wavelength dependent transmission responsive device to determine one or more distinct wavelength points in the sweep of the illumination source, and
    a measuring circuit synchronized to the wavelength dependent transmission responsive device to measure illumination from the device under test over at least a range of the wavelength band.

2. The instrument of claim 1, said wavelength dependent transmission responsive device comprising a gas cell.

3. The instrument of claim 1, said wavelength dependent transmission responsive device comprising a Fabry Perot device.

4. A method of testing an object using electromagnetic energy, comprising
    illuminating the object using electromagnetic energy while sweeping the electromagnetic energy over a range of wavelengths,
    measuring electromagnetic energy from the object in response to such illuminating,
    determining one or more distinct wavelength points using a wavelength dependent transmission responsive device to which the electromagnetic energy is directed,
    coordinating the measuring step with one or more of the distinct wavelength points of the sweep determined by the wavelength dependent transmission responsive device.

5. The method of claim 4, said coordinating comprising directing electromagnetic energy through a gas cell.

6. The method of claim 4, said coordinating comprising directing electromagnetic energy to a Fabry Perot device.

7. A system for measuring electromagnetic energy from a device under test that is illuminated with electromagnetic energy at a wavelength that is swept over a range of way lengths, comprising
    a measuring system for measuring electromagnetic energy from the device under test, and
    a periodic wavelength reference having a detectable distinct response to a distinct wavelength of such electromagnetic energy to indicate to the measuring system occurrence of such distinct wavelength as a reference point to synchronize measurements with the sweeping of the wavelength of the electromagnetic energy.

8. The system of claim 7, said reference comprising a gas.

9. The system of claim 7, said reference comprising a Fabry Perot device.

10. The system of claim 7, further comprising a source of electromagnetic energy and wherein the wavelength of the source is swept in a known way over a range of wavelengths.

* * * * *

UNITED STATES PATENT AND TRADEMARK OFFICE
CERTIFICATE OF CORRECTION

PATENT NO. : 6,847,439 B2
DATED : January 25, 2004
INVENTOR(S) : Minneman et al.

It is certified that error appears in the above-identified patent and that said Letters Patent is hereby corrected as shown below:

Column 8,
Line 50, replace "time to" with -- time t0 --

Column 12,
Lines 3-4, replace "way lengths" with -- wavelengths --

Signed and Sealed this

Twelfth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,847,439 B2
DATED : January 25, 2005
INVENTOR(S) : Manning

Page 1 of 1

It is certified that error appears in the above-identified patent and that said Letters Patent is hereby corrected as shown below:

Column 8,
Line 50, replace "time to" with -- time t0 --

Column 12,
Lines 3-4, replace "way lengths" with -- wavelengths --

This certificate supersedes Certificate of Correction issued April 12, 2005.

Signed and Sealed this

Fifth Day of July, 2005

JON W. DUDAS
*Director of the United States Patent and Trademark Office*